United States Patent

Schlangen

[11] Patent Number: 5,618,282
[45] Date of Patent: Apr. 8, 1997

[54] REMOVAL AIDS FOR ADHESIVELY SECURED ABSORBENT ARTICLES

[75] Inventor: Karen S. Schlangen, Appleton, Wis.

[73] Assignee: Kimberly-Clark Corporation, Neenah, Wis.

[21] Appl. No.: 539,519

[22] Filed: Oct. 16, 1995

[51] Int. Cl.⁶ .................................................. A61F 13/15
[52] U.S. Cl. .............................................................. 604/387
[58] Field of Search ........................................ 604/387, 904, 604/284

[56] References Cited

U.S. PATENT DOCUMENTS

| | | | |
|---|---|---|---|
| 2,924,331 | 2/1960 | Hoey | 206/63.2 |
| 2,940,868 | 6/1960 | Patchell | 117/38 |
| 3,452,752 | 7/1969 | DeCrescenzo | 604/904 |
| 3,688,771 | 9/1972 | Werner | 604/387 |
| 3,811,438 | 5/1974 | Economou | 128/156 |
| 3,885,559 | 5/1975 | Economou | 128/156 |
| 4,072,151 | 2/1978 | Levine | 128/290 R |
| 4,266,546 | 5/1981 | Roland | 604/904 |
| 4,609,373 | 9/1986 | Johnson | 604/387 |
| 4,641,643 | 2/1987 | Greer | 128/156 |
| 4,666,441 | 5/1987 | Andriola et al. | 604/897 |
| 4,753,648 | 6/1988 | Jackson | 604/389 |
| 4,900,320 | 2/1990 | McCoy | 604/387 |
| 4,917,675 | 4/1990 | Taylor et al. | 604/385.1 |
| 4,925,453 | 5/1990 | Kannankeril | 604/378 |
| 5,128,187 | 7/1992 | Polski | 604/387 |
| 5,336,208 | 8/1994 | Rosenbluth | 604/387 |
| 5,417,224 | 5/1995 | Petrus | 604/904 |

FOREIGN PATENT DOCUMENTS 2574286  6/1986  France .................................. 604/387

*Primary Examiner*—Michael J. Milano
*Attorney, Agent, or Firm*—Mark L. Davis

[57] ABSTRACT

The present invention relates to an absorbent article adapted to be secured to a wearer's body. The absorbent article has a cover disposed toward the bodyfacing surface and a baffle disposed toward the undergarment-facing surface. Positioned between the cover and the baffle is an absorbent material. An adhesive is secured to the bodyfacing surface to hold the absorbent article in intimate contact with the wearer during use. The absorbent article further includes a detaching device for disengaging the absorbent article from the wearer's body when removal is desired. The detaching device, which may have a portion thereof elastomeric, includes a separate strip of material having spaced apart ends. The ends are secured ends to at least one surface of the absorbent article, i.e., the bodyfacing surface, garment-facing surface or both. The medial portion of the strip is unattached forming an open area between the baffle and the separate strip material for grasping and hygienically removing the absorbent article.

15 Claims, 4 Drawing Sheets

REMOVAL AIDS FOR ADHESIVELY SECURED ABSORBENT ARTICLES

BACKGROUND OF THE INVENTION

The present invention relates to the field of disposable absorbent articles adapted to be secured to a portion of a wearer's body and utilized for the absorption and containment of body fluids such as menstrual fluid, urine and other body exudates. More particularly, the present invention relates to removal aids for comfortably disengaging the disposable absorbent article from the wearer's body.

Disposable absorbent articles for the absorption and containment of urine, menses and other body exudates are generally known in the art. Such disposable articles have found particular utility in the fields of infant, child, feminine and adult incontinence hygiene. In the area of feminine care, such disposable absorbent articles have been commercialized in two basic types, the tampon and the sanitary napkin. For the purposes described herein, sanitary napkins includes thin absorbent devices such as a panty liner and an interlabial device, which may have an absorbency of just a few grams, to the larger maxi and overnight pad designed for absorbing a much greater quantity of body fluids. Present sanitary napkins are unitary, preshaped and prefolded and may be individually packaged for discreteness and hygienic purposes. Their construction is comprised of a liquid permeable, bodyside cover; a liquid-impermeable, garment-facing baffle and an absorbent positioned between the cover and the baffle. The sanitary napkin also may include an adhesive disposed on the garment-facing surface of the baffle to secure the sanitary napkin in the crotch region of the wearer's undergarment.

After the sanitary napkin is soiled, it is removed and discarded. Removing a sanitary napkin secured to the undergarment usually involves stripping the sanitary napkin from the crotch area of the undergarment. However, if the sanitary napkin has become adhered to the wearer the sanitary napkin may pull the pubic hair and tissue from the person as it is being removed, causing, in most cases, an extreme amount of discomfort.

A sanitary napkin is disclosed in the patent application having U.S. Ser. No. 08/167,597 filed on Dec. 14, 1993, the entire disclosure of which is incorporated herein by reference, utilizes a body adhesive to secure the sanitary napkin to the wearer's body. To remove this sanitary napkin, the wearer usually grasps an exposed edge of the sanitary napkin and pulls downward. Depending upon the location of the adhesive, grasping an edge may be difficult. The adhesive may also have body fluids, such as menses or other fluids coating its surface. Desirably, the wearer wants to avoid contacting the body excretions to prevent soiling her hands and possibly her clothing. Touching the adhesive may also block the that portion of the adhesive, lessening the adhesive strength for retaining the sanitary napkin against the body if reapplied.

Therefore, there is a need for a means to comfortably and hygienically remove such an absorbent article from the wearer's body without soiling the person or their clothing.

SUMMARY OF THE INVENTION

Briefly, the present invention relates to an absorbent article adapted to be secured to a wearer's body. The absorbent article has a liquid-permeable, bodyfacing surface and a liquid-impermeable, garment-facing surface. Positioned between the bodyfacing surface and the garment-facing surface is an absorbent material. An adhesive is secured to the bodyfacing surface to hold the absorbent article in intimate contact with the wearer during use. The absorbent article further includes a detaching device for disengaging the absorbent article from the wearer's body when removal is desired. The detaching device includes a separate strip of material having spaced apart ends. The ends are secured to at least one surface of the absorbent article, i.e., the bodyfacing surface, garment-facing surface or both. The medial portion of the strip is unattached forming an open area between the garment-facing surface and the strip material. The medial portion is utilized for grasping and removing the absorbent article. Unexpectedly, it has been discovered that removal of the absorbent article can be simplified if the force applied to remove the absorbent article is initially at a proper angle relative to the wearer's body and the adhesive on the pad. The detaching device aids the wearer in comfortably removing the absorbent article by initially establishing the proper angle, alpha ($\alpha$), between the body of the wearer and the adhesive.

It is a general object of the invention to provide a removal aid for comfortably detaching an adhesively secured absorbent article from a wearer's body. More specifically, it is an object of the invention to provide a removal aid on the absorbent article that permits the wearer to remove it with one hand.

It is another object of the invention to provide a sanitary napkin which is adhesively secured to the body and which incorporates a detaching device positioned on the baffle for protecting the user from contacting body fluids when removing the sanitary napkin.

These and other objects of the invention will be more readily apparent when considered in reference to the following description when taken in conjunction with the accompanying drawings.

DETAILED DESCRIPTION OF THE PREFERRED EMBODIMENT

The present invention relates generally to a disposable absorbent article which is secured to a wearer's body by a pressure sensitive body adhesive. For convenience of description only, the invention will be described as a catamenial device, i.e. a sanitary napkin, but is not limited thereto. It is to be understood that the invention may be adapted for use in other absorbent articles such as diapers, incontinent devices, adhesive bandages and the like which incorporate some means for adhesively adhering the absorbent article to at least a portion of a wearer's body.

Figure 1:
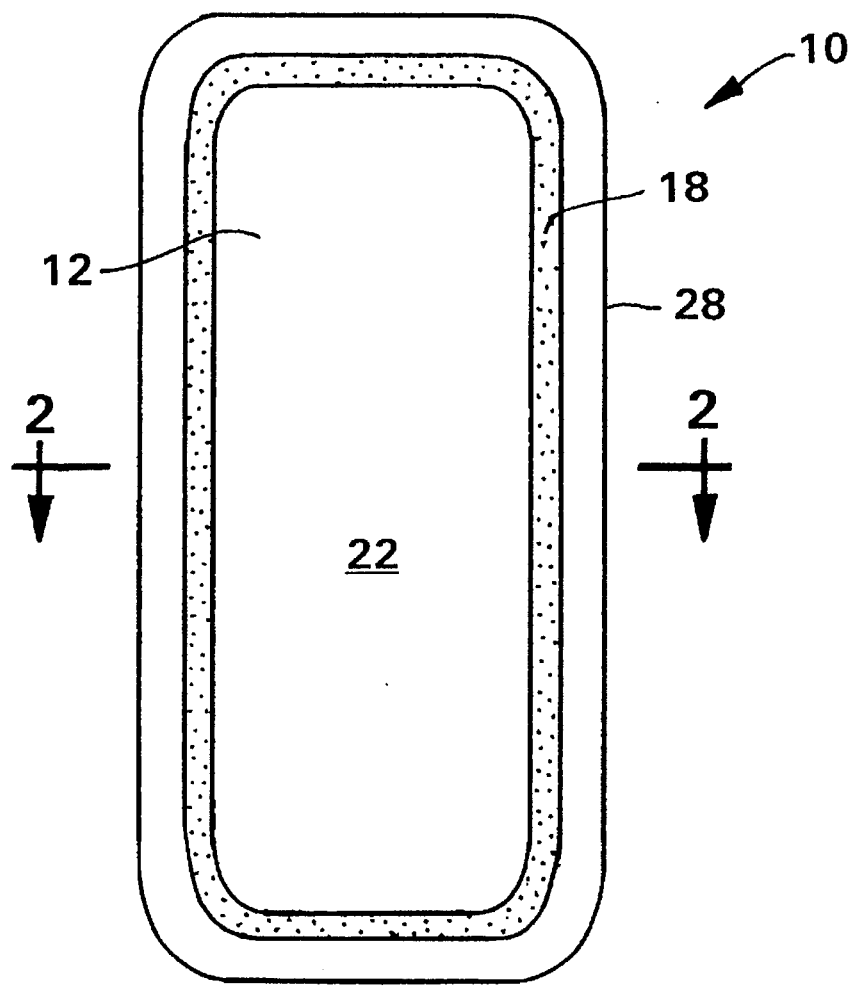
FIG. 1 is a top view of an absorbent article which may be secured to the wearer's body during use.
Figure 2:
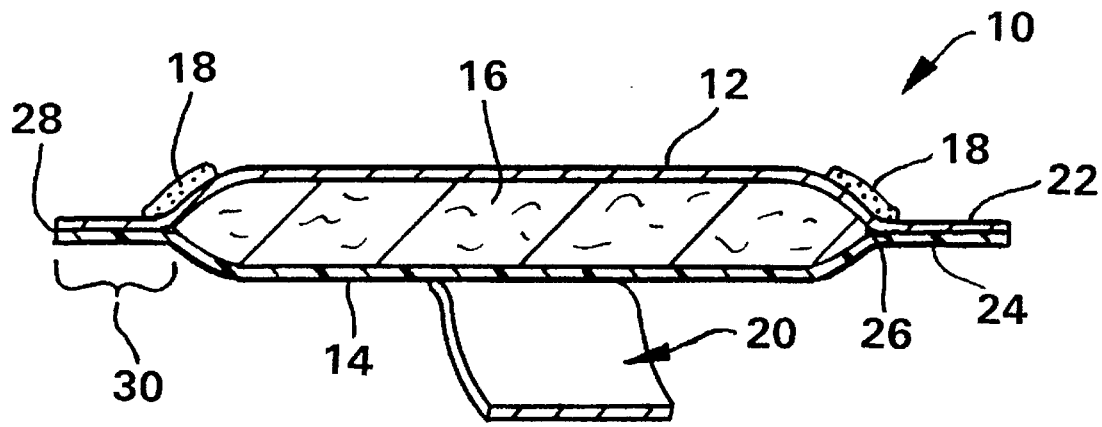
FIG. 2 is a cross-sectional view of FIG. 1 taken along line 2—2.

For ease of understanding, when referring to the Figures, the same numeral designates the same part in the different views and embodiments. Referring to FIGS. 1 and 2, an embodiment of a sanitary napkin 10 is shown. The sanitary napkin 10 typically includes a fluid-permeable, bodyfacing surface 12; a fluid-impermeable, garment-facing surface 14; an absorbent 16 disposed between the bodyfacing surface 12 and the garment-facing surface 14; and an adhesive 18 secured to the bodyfacing surface 12 for adhering the sanitary napkin 10 to a wearer's body during use. A detaching device 20, partially illustrated in FIG. 2, is affixed to the sanitary napkin 10 to provide an easy means for comfortably disengaging the sanitary napkin 10 from the wearer's body. The sanitary napkin 10 can also include a peel strip, not shown, overlying the adhesive 18 to prevent the adhesive from becoming contaminated and/or prematurely adhering to an unintended surface. Suitable materials for use as a peel strip are commercially available from a number of sources.

As illustrated, the sanitary napkin 10 has a racetrack shape, but is not limited thereto. It can also be hourglass, oval or any other configuration that will allow the sanitary napkin 10 to come into intimate contact with the wearer. As used herein, the term "sanitary napkin" refers to an article which is worn by females adjacent to the pudendal region and which is intended to absorb and contain various exudates which are discharged from the body such as blood, menses, and urine, and which is intended to be discarded when soiled, not laundered and reused. Interlabial devices which reside partially within and partially external of the female wearer's vestibule are also within the scope of this invention.

Referring to FIG. 2, the bodyfacing surface 12 is generally integral to and associated with one surface of a cover 22 and the undergarment-facing surface 14 is generally integral to and associated with one surface of a baffle 24. The cover 22 and baffle 24 can have a length and a width dimension extending beyond an absorbent edge 26 in a contiguous relationship and are sealed together to define a periphery 28 of the sanitary napkin 10. The portion from the absorbent edge 26 to the periphery 28 is defined herein as the peripheral seal 30. The absorbent 16 is thereby enclosed between the cover 22 and the baffle 24. The cover 22 and the baffle 24 may be sealed together using any suitable means that will not leave a hard, uncomfortable residue that may be annoying to the wearer. As used herein, the term "sealed" encompasses configurations whereby the cover 22 is directly joined to baffle 24 and configurations whereby the cover 22 is indirectly joined to the baffle 24 by affixing the cover 22 to an intermediate member, which are in turn affixed to the baffle 24. Methods for attaching the cover 22 and baffle 24 are well known to those skilled in the art and include the use of hot melt adhesives, pressure-sensitive adhesives, double-sided tape, sonic bonding and heat sealing.

The cover 22 is designed to contact the body of the wearer and therefore should be easily penetrated by body fluids, non-irritation to the wearer's skin and preferably does not absorb an appreciable amount of fluid. The cover 22 can be constructed of a woven or nonwoven, natural or synthetic material. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net material, also work well. Particularly preferred are composite materials of a polymer and a nonwoven fabric material. Still another cover material is a spunbond web of polypropylene. The web can contain about 1% to about 6% titanium dioxide pigment to give it a clean, white appearance. A uniform spunbond material is desirable because it has sufficient strength in the longitudinal direction, even after being perforated, to resist being torn or pulled apart during use. The most preferred polypropylene webs have a weight of between about 18 and 40 grams per square meter. An optimum weight is between about 30 and about 40 grams per square meter.

To aid in the penetration of the liquid through the web, the cover 22 can also be treated with a surfactant to improve its hydrophilic characteristics. The surfactant can include topical additions or internally applied materials like polysiloxanes.

The baffle 24 acts as a barrier between the absorbed body fluids contained in the absorbent 16 and the person wearing the sanitary napkin 10. Accordingly, the baffle 24 is nonabsorbent and is impervious to liquids. The baffle 24 should be soft and compliant since a portion of the baffle 24 may reside adjacent the thigh region of the wearer. As used herein, the term "compliant" refers to materials which will readily conform to the general external shape and contours of the human anatomy. In a preferred embodiment, the baffle 24 may permit the passage of air or vapor out of the sanitary napkin 10 while blocking the passage of liquids from the absorbent 16. A good baffle material is a micro-embossed, polymeric film, such as polyethylene or polypropylene. Bicomponent films can also be used as well as woven and nonwoven fabrics which have been treated to render them liquid-impermeable. The baffle 24 may also be made from a polyethylene film having a thickness in the range of from about 0.012 mm to about 1.0 mm.

The absorbent 16 is in liquid communication with the bodyfacing surface 12 and is positioned between the bodyfacing surface 12 and the garment-facing surface 14. The term "liquid communication" means that body fluid insulting the bodyfacing surface 12 will, substantially, be absorbed by the absorbent 16. Referring again to FIG. 2, the cover 22 and the baffle 24 in combination enclose the absorbent 16, substantially defining the absorbent's perimeter or edge 26. The materials used in the absorbent 16 are designed to absorb body exudates, including menstrual fluids, blood and urine. Suitable materials include wood pulp fluff, rayon, cotton and meltblown polymer, such as polyester, polypropylene or coform. Coform is an air-formed combination of meltblown polymers, such as polypropylene, and absorbent staple fibers, such as cellulose. A preferred material is wood fluff, for it is low in cost, relatively easy to form and has good absorbency. The absorbent 16 may be a composite comprised of a hydrophilic material that can be formed from various natural or synthetic fibers, wood pulp fibers, regenerated cellulose or cotton fibers, an airlaid tissue or a blend of pulp and other fibers. The absorbent 16 can be made from other well known materials used in absorbent articles, including multiple layers of cellulose wadding, rayon fibers, cellulose sponge, hydrophilic synthetic sponge, such as polyurethane, and the like. The capacity of the absorbent 16 may be varied depending upon the intended usage of the final product.

The sanitary napkin 10 may also include other layers, such as a wicking layer, one or more tissue layers and may contain superabsorbent in combination with one or more other absorbent materials described above, none of which are shown in the Figures. Such layers and materials are commercially available from several sources and are well known to those skill in construction of disposable absorbent articles, such as sanitary napkins, diapers and incontinent devices.

The adhesive 18 is positioned on the bodyfacing surface 12 to contact the wearer and support the sanitary napkin 10 during use. As shown in FIG. 2, the adhesive 18 is adhered to the cover 22. The adhesive 18 can overlie from about 5 percent to about 95 percent of the bodyfacing surface 12. Preferably, the adhesive 18 overlies from about 5 percent to about 75 percent of the bodyfacing surface 12, more preferably, from about 5 percent to about 35 percent and most preferred, from about 5 percent to about 20 percent of the bodyfacing surface 12. Suitable adhesive materials are disclosed in the commonly assigned patent application having U.S. Ser. No. 08/331,072 filed on Oct. 28, 1994, the entire disclosure of which is incorporated herein by reference and made a part hereof.

In an alternative configuration not shown, the baffle 24 may overwrap a portion of the cover 22 along the absorbent edge 26 so that a portion of the bodyfacing surface 12 would be comprised of the liquid-permeable cover 22 and a portion would be comprised of the liquid-impermeable baffle 24. In this configuration, the adhesive 18 may reside on the cover 22, the baffle 24 or both.

Figure 3:
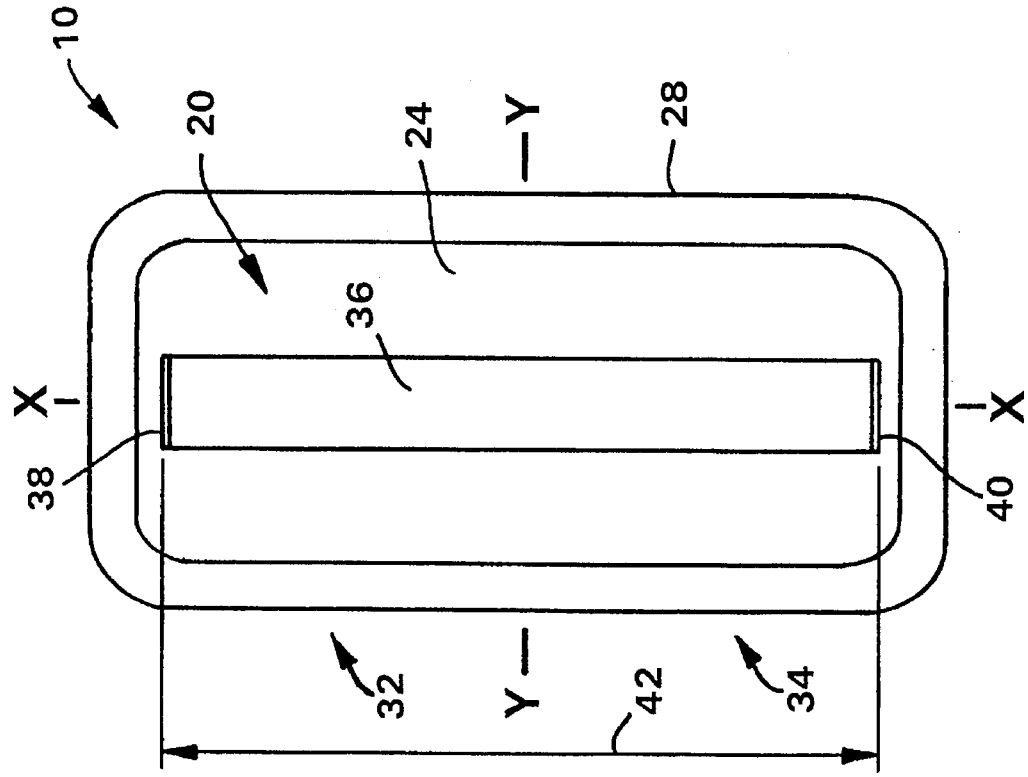
FIG. 3 is a bottom view of the absorbent article illustrating the detaching means of the invention.

Referring to FIG. 3, the sanitary napkin 10 is transversely divided along line Y—Y into a first portion 32 and a second portion 34 which are substantially equal in size. The detaching device 20 is formed from an elongate strip of material 36 having a first end 38 and a distally spaced second end 40. The first and second ends 38 and 40 are positioned in the first and second portions 32 and 34, respectively and are affixed to at least one surface of the sanitary napkin 10. As shown in FIG. 3, the first and second ends 38 and 40 are affixed to the garment-facing surface 14. The first and second ends 38 and 40 can be secured to the sanitary napkin 10 along the peripheral seal 30 and desirably, are affixed inward from the peripheral seal 30. A medial grasping portion 42 lies between the first end 38 and the second end 40. The medial grasping portion 42 is unsecured, forming an opening for grasping the elongate strip 36. The detaching device 20 provides a means by which the sanitary napkin 10 can be comfortably and hygienically removed. The detaching device 20 also permits the soiled sanitary napkin 10 to be hygienically handled during toileting and disposal.

Figure 4:
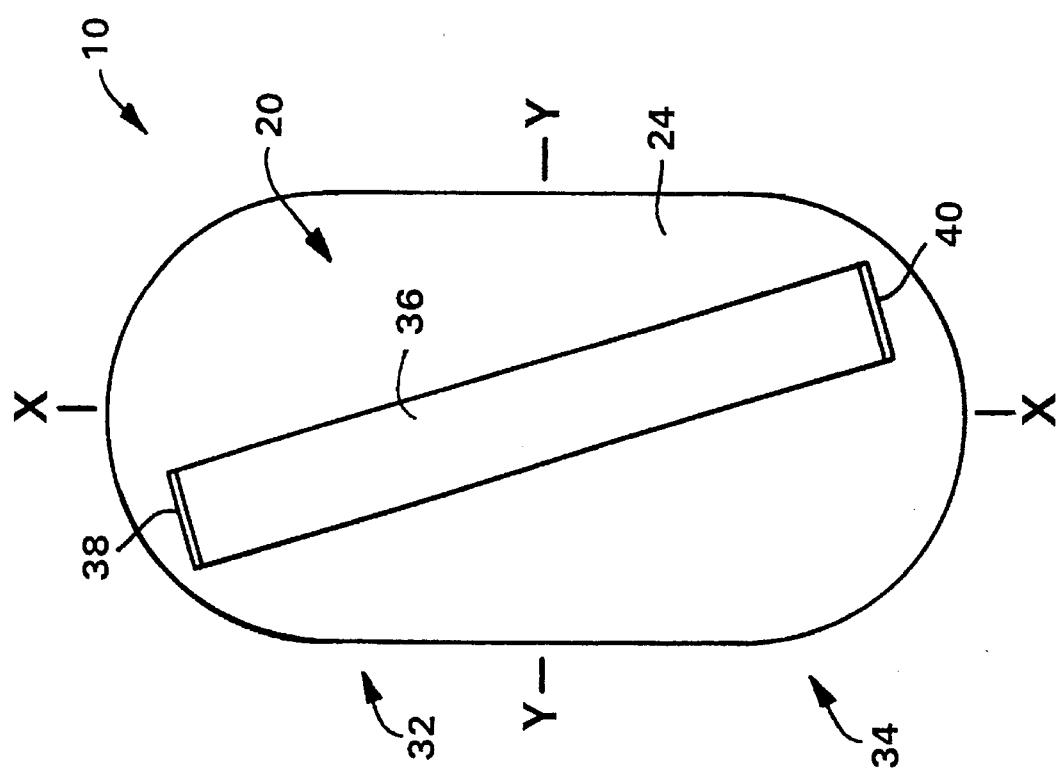
FIG. 4 is a bottom view of an absorbent article illustrating an alternative embodiment of the detaching means of the invention.

As illustrated in FIG. 3, the elongate strip 36 is secured to the baffle 24 and is symmetrically aligned along a central longitudinal axis X—X of the sanitary napkin 10. However, the elongate strip 36 is not limited to this configuration. Referring to FIG. 4, the elongate strip 36 can be skewed relative to the longitudinal axis, X—X, the transverse axis Y—Y, or both so that the elongate strip 36 diagonally traverses the length of the sanitary napkin 10. Other configurations, not shown, include using two or more elongate strips secured to at least one of the surfaces 12 and 14 in various patterns, such as "X" or "+" are also within the scope of the invention.

The elongate strip 36 may be composed of any material that can be affixed to the desired surface. The elongate strip 36 should have a modulus greater than the peel strength of the adhesive 18 to prevent the elongate strip 36 tearing during removal. Suitable materials include bonded carded webs of polyester, polypropylene, polyethylene, nylon, or other heat-bondable fibers, polymeric film, such as polyethylene or polypropylene. Desirably, the material has at a portion that is at partially elastomeric permitting the elongate strip 36 to stretch in at least one direction when stressed (pulled) by a force of less than about 1000 grams to a length greater than its length in a relaxed state. Preferably, the elongate strip 36 can stretch to a length greater than about 5 percent than its relaxed state, and more preferably the strip 36 will stretch to a length ranging from about 5 percent to about 80 percent greater than its relaxed state. The elasticity of the material may be determined by any technique that substantially isolates two ends of a predetermined amount of material. The isolated material is pulled with a force up to 1000 grams and the elongation is then measured. By the material having elastomeric properties, the detaching device 20 can reside substantially flat against the garment-facing surface 14 during use, reducing the likelihood of the sanitary napkin 10 and 100 shifting while being worn and which also allows the wearer to be active without affecting the comfort and fit of the sanitary napkin 10 and 100. The term "elastomeric" as used herein means that the material will stretch when force is applied in at least one direction, preferably along the length, to greater than about 5 percent of its unstressed state and will return to substantially its relaxed dimension(s) when the force is removed.

Figure 5:
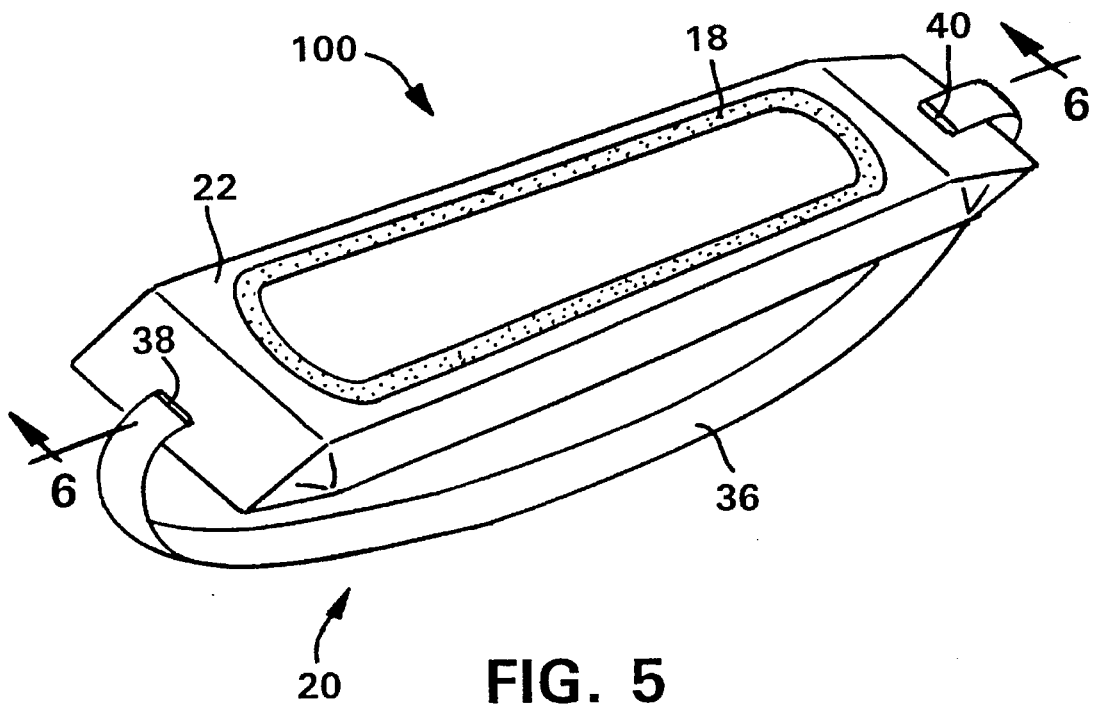
FIG. 5 is a perspective view of another embodiment of an absorbent article of the invention.
Figure 6:
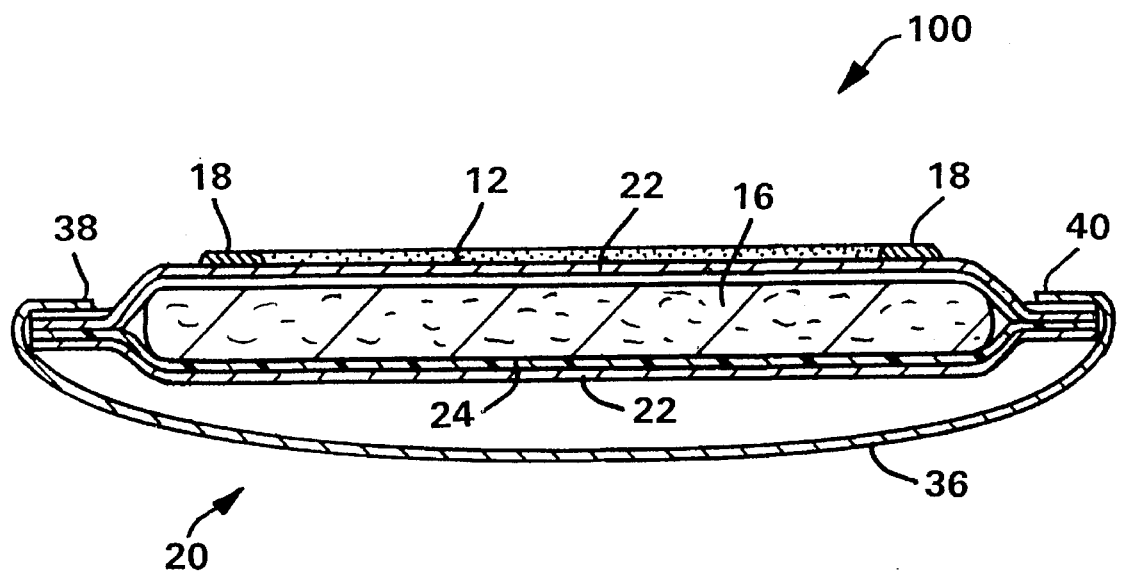
FIG. 6 is a cross-sectional view taken along line 6—6 of FIG. 5.

Referring to FIGS. 5 and 6, a sanitary napkin 100 is shown which is similar to the sanitary napkin 10 except the cover 22 encloses the absorbent 16 to produce what is know in the art as a wrapped pad. The construction of the wrapped pad is described in greater detail in the U.S. Pat. No. 4,200,103 issued on Apr. 29, 1980, the disclosure of which is incorporated herein by reference and made a part hereof. The first and second ends 38 and 40 of the elongate strip 36 are secured to the cover 22 at any location that does not substantially interfere with the ability of the adhesive 18 to support the sanitary napkin 100 during use.

Figure 7:
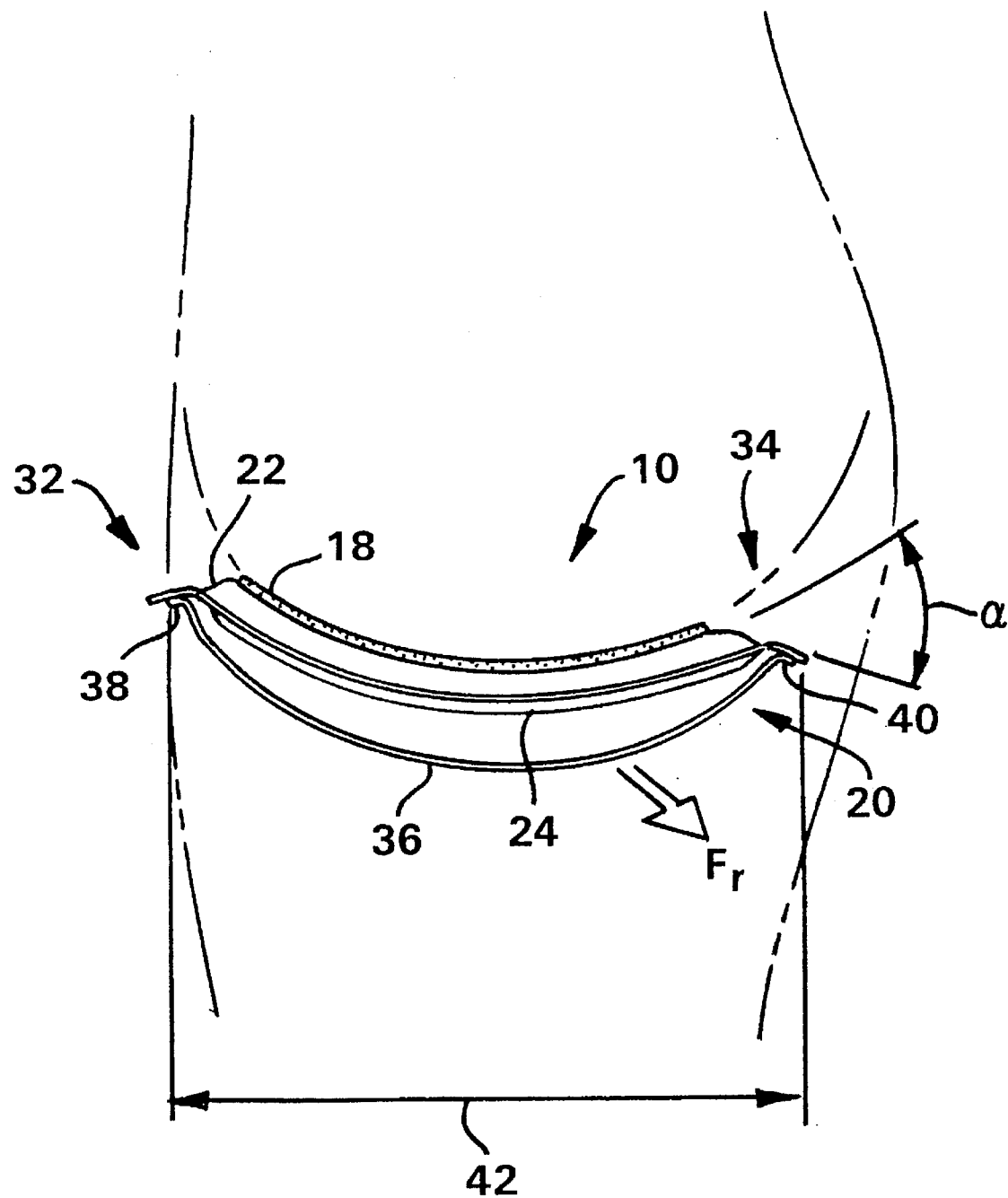
FIG. 7 is a side view of the sanitary napkin illustrating an angle alpha formed between the wearer and the surface of the sanitary napkin when the sanitary napkin is being removed.

Referring to FIG. 7, the wearer can remove or disengage the sanitary napkin 10 from the body by grasping the grasping portion 42 of the elongate strip 36 and pulling it directionally away from the body. The detaching device 20 distributes the outward removal force, $F_r$, along the elongate strip 36, initially directing the removal force $F_r$ so that an acute angle $\alpha$ is formed between the wearer's body, shown in phantom, and the adhesive 18. This allows the first and second portions 32 and 34 to be substantially simultaneously disengaged from the body. Preferably, the detaching device 20 initially directs the outward removal force $F_r$ so that the angle $\alpha$ is less than 45 degrees. It has unexpectedly been discovered that by initially directing the removal force in this manner, the sanitary napkin 10 can be comfortably removed from the wearer's body.

The foregoing detailed description has been for the purpose of illustration setting forth the preferred embodiment of the invention. Accordingly, a number of modifications and changes may be made without departing from the spirit and scope of the present invention. Therefore, the invention should not be limited by the specific terms employed, but only by the claims.

We claim:

1. An absorbent article adapted to be adhesively secured to a wearer's body, said absorbent article comprising:
   a. a liquid-permeable cover having a bodyfacing surface;
   b. a liquid-impermeable baffle having a garment-facing surface;
   c. an absorbent positioned between said bodyfacing surface and said garment-facing surface, said absorbent having an edge and said cover and said baffle extending beyond said edge to form a peripheral seal;
   d. adhesive means for securing said absorbent article to the wearer's body, said adhesive means being affixed to said bodyfacing surface; and e. detaching means for disengaging said absorbent article from the wearer's body when removal of the absorbent article is desired, said detaching means including a longitudinal elongate strip with a first end and a spaced apart second end, said spaced apart ends being secured to said bodyfacing surface of said cover, said elongate strip further including an unsecured medial grasping portion positioned between said spaced apart ends for grasping and removing said absorbent article.

2. The absorbent article of claim 1 wherein said first and second ends are secured to said cover along said peripheral seal.

3. The absorbent article of claim 1 wherein said first and second ends are secured to said cover inward from said peripheral seal.

4. The absorbent article of claim 1 having a transverse axis, said transverse axis dividing said absorbent article into a first portion and a second portion of substantially equal size, said first end being secured to said bodyfacing surface of said cover in said first portion and said second end being secured to said bodyfacing surface of said cover in said second portion.

5. The absorbent article of claim 1 wherein said elongate strip is non-elastic.

6. The absorbent article of claim 1 wherein said elongate strip is elastomeric.

7. The absorbent article of claim 1 wherein said detaching means distributes an outward removal force along said elongate strip so that an acute angle $\alpha$ is formed between the wearer's body and said adhesive means.

8. An absorbent article adapted to be adhesively secured to a wearer's body, said absorbent article comprising:

a. a liquid-permeable cover having a bodyfacing surface;

b. a liquid-impermeable baffle;

c. an absorbent enclosed between said cover and said baffle, said absorbent having an edge and said cover and said baffle extending beyond said edge to form a peripheral seal;

d. adhesive means for securing said absorbent article to the wearer's body, said adhesive means being affixed to said bodyfacing surface; and e. detaching means for disengaging said absorbent article from the wearer's body when removal of the absorbent article is desired, said detaching means including a longitudinal elongate strip with a first end and a spaced apart second end, said absorbent article including a transverse axis dividing said absorbent article into a first portion and a second portion of substantially equal size, said first end being secured to said baffle in said first portion and said second end being secured to said baffle in said second portion, said elongate strip further including an unsecured medial grasping portion positioned between said spaced apart ends for grasping and removing said absorbent article.

9. The absorbent article of claim 8 wherein said first and second ends being secured to said baffle inward from said peripheral seal.

10. The absorbent article of claim 8 wherein said elongate strip is elastomeric.

11. A sanitary napkin adapted to be adhesively secured to a wearer's body, said sanitary napkin comprising:

a. a liquid-permeable cover having a bodyfacing surface;

b. a liquid-impermeable baffle;

c. an absorbent enclosed between said cover and said baffle, said absorbent having an edge and said cover and said baffle extending beyond said edge to form a peripheral seal;

d. adhesive means for securing said sanitary napkin to the wearer's body, said adhesive means being affixed to said bodyfacing surface; and e. detaching means for disengaging said sanitary napkin from the wearer's body when removal of the sanitary napkin is desired, said detaching means including a longitudinal elongate strip with a first end and a spaced apart second end, at least a portion of said elongate strip being elastomeric, said sanitary napkin including a transverse axis dividing said sanitary napkin into a first portion and a second portion of substantially equal size, said first end being secured to said cover in said first portion and said second end being secured to said cover in said second portion, said elongate strip further including an unsecured medial grasping portion positioned between said spaced apart ends for grasping and removing said sanitary napkin.

12. The sanitary napkin of claim 11 wherein said elongate strip can stretch to a length of about 5 percent to about 80 percent greater than in its relaxed state.

13. The sanitary napkin of claim 11 wherein said first and second ends are secured to said cover along said peripheral seal.

14. The sanitary napkin of claim 11 wherein said detaching means distributes an outward removal force along said elongate strip so that an acute angle $\alpha$ is formed between a wearer's body and said adhesive means.

15. The detaching means of claim 13 wherein said angle $\alpha$ is less than 45 degrees.

\* \* \* \* \*